United States Patent [19]

Pezzoli et al.

[11] 4,370,444

[45] Jan. 25, 1983

[54] CONCENTRATED AQUEOUS SOLUTION OF PHENOL AND FORMALDEHYDE STABLE AT LOW TEMPERATURE PROCESS FOR PREPARING SAME

[75] Inventors: Silvestro Pezzoli, Biassono; Giancarlo Rossi, Monza, both of Italy

[73] Assignee: Societa Italiana Resine S.I.R. S.p.A., Milan, Italy

[21] Appl. No.: 272,622

[22] Filed: Jun. 11, 1981

[30] Foreign Application Priority Data

Jun. 11, 1980 [IT] Italy .............................. 22698 A/80

[51] Int. Cl.³ .............................................. C08L 5/00
[52] U.S. Cl. .................................... 524/732; 524/47; 524/56; 524/58; 524/734
[58] Field of Search ................ 260/17.2, 29.3, 45.7 R; 524/732, 734, 56, 58, 47

[56] References Cited

U.S. PATENT DOCUMENTS 4,020,027 4/1977 Nicholas et al. .................... 260/17.2
4,058,403 11/1977 Funabiki et al. .................... 260/17.2

*Primary Examiner*—Theodore E. Pertilla
*Attorney, Agent, or Firm*—Sughrue, Mion, Zinn, Macpeak & Seas

[57] ABSTRACT

Aqueous solutions of phenol and formaldehyde are stabilized with at least one carbohydrate such as saccharose, glucose, fructose, maltose, starch hydrolysates or molasses. The solutions are condensable and usable for preparing A-stage phenolic resin (resols).

7 Claims, No Drawings

CONCENTRATED AQUEOUS SOLUTION OF PHENOL AND FORMALDEHYDE STABLE AT LOW TEMPERATURE PROCESS FOR PREPARING SAME

"A-Stage" phenolic resins (resols) such as those used for impregnation of Kraft paper in the manufacture of decorative laminates, are usually prepared by condensing phenol and formaldehyde in aqueous medium in the presence of a condensing agent such as sodium hydroxide. To this end, phenol and a solution of formaldehyde (typically containing a stabilizer such as methanol) are used as separate "feeds" or starting materials, and some substantial disadvantages of this technique will be pointed out hereinafter. Accordingly, it is an object of this invention to provide an aqueous solution containing both phenol and formaldehyde at a substantial concentration and in a form fully available for their condensation reaction, said solution being flowable, homogeneous and clear at low temperatures (from room temperature to, even, 0° C.) and being stable for a considerable period of time at least at temperatures not substantially lower than 10° C., so that the solution may be successfully stored, transported and used in lieu of the separate reactants for making "A-stage" resins.

In accordance with the above, this invention provides an aqueous, fluid, storage-stable solution of phenol, formaldehyde and a stabilizer, wherein: the molar ratio of the phenol to the formaldehyde is from 0.5:1 to 1.3:1; the water content does not exceed 30% by weight; the stabilizer comprises a carbohydrate or a mixture of carbohydrates in a proportion of 1–10% by weight; the solution being free from purposely added acids and bases and its content of any genetic formic acid being not greater than 0.04% by weight.

The solution may incidentally contain very small amounts of "endogenous" condensation products due to a correspondingly small degree of condensation of the phenol and formaldehyde present, but it was found that the monomers forming such products are equally available in the use of the solution (condensation to the resol stage). Therefore, unless stated otherwise, the proportions of phenol and formaldehyde as indicated hereinbefore and the amounts which will be indicated hereinafter shall be understood as including these monomers both in their free and bound form. The carbohydrates used as stabilizers are believed to take part in the resol-forming condensation reaction; any way, they do not adversely affect the characteristics of the resol.

The term "genetic formic acid" is to be understood as denoting any formic acid which may originally be present in the aqueous solution of formaldehyde used for preparing the solution according to the invention, and also any formic acid formed in the solution due to reactions of Cannizzaro type. As long as the amounts of genetic formic acid in the solution do not exceed 0.04% by weight, any small amounts of condensation products produced thereby do not impair the stability and, in use of the solution, apparently behave as the two separate constituents of which they are composed.

The amount water in the solution shall be understood as the difference to 100 of the joint weight of the phenol, formaldehyde and carbohydrate(s) in the solution.

The stabilizer may be an ordinary carbohydrate or sugar as saccharose, glucose, fructose and maltose, both individually or in mutual mixtures and occasionally also in mixture with polysaccharides. All these substances are relatively little expensive, readily dissolve in water and exert their stabilizing effect on the phenol/formaldehyde solution permitting preservation of the latter at low temperatures. It is possible to use a single carbohydrate as well as a mixture of carbohydrate both in pure form and in form of products or by-products of industrial manufacture of sugars, such as molasses, and also in form of hydrolysates of maize and similar.

In the preferred solutions of this invention the molar ratio phenol/formaldehyde is in the range of 0.55:1 to 0.75:1, the water being present in amounts from 20 to 30% by weight, while the amount of the stabilizing carbohydrate is selected depending on the temperature at which the solution is to be preserved. Thus, in case of preservation at temperatures proximal to 0° C. the stabilizer is used in amounts proximal to the upper limit of the range stated hereinbefore, while in the case of preservation at room temperature (20°–25° C.) it is possible to use the lowest proportions in the said range.

For what concerns the content of water in the solution according to this invention it is not convenient to lower it below about 20% by weight, in order to avoid the use of excessively concentrated formalins in the preparation of solution. The maximum value of the water content is not critical, but it is not generally advisable to exceed values of about 30 percent by weight, thereby to not loose the advantages arising from high concentrations of phenol and formaldehyde. According to a preferred embodiment, the weight ratio formaldehyde/water is 1:1 or is close to this value, so that the "A-stage" resin may be prepared from the solution without removal of any excess water and, accordingly, under avoidance of pollution problems arising from effluent waters polluted by the presence of phenol and formaldehyde.

The use of the solution according to the present invention, besides the advantages related to the preparation of phenolic resol resins, offers also advantages in the storage and in the transport in comparison with the single constituents.

By way of example, phenol is solid at room temperature and it is usual to maintain it in liquid condition during storage and transport by heating the tanks which contain it. Obviously, this involves expenditure of heat.

Moreover it is known in the art to use, as formaldehyde sources, aqueous solutions at elevated concentration, for example 50% by weight, of paraformaldehyde. However, such aqueous solutions present difficulties relating to their preservation, due to the tendency to form at room temperature insoluble polymers. It is therefore necessary to use stabilizers and/or effect the preservation at temperatures higher than the room one, and usually at temperatures from 30° to 55° C., depending upon the concentration of the solution. On the other hand, paraformaldehyde entails a cost of its obtention from aqueous formaldehyde, is more difficult to handle as such due to its solid nature and its reactivity tends to decrease with time. Therefore, concentrated aqueous solutions according to the present invention certainly represent considerable practical advantages.

The preparation of a solution according to the present invention involves dissolving the ingredients under specific conditions. Molten phenol is advantageously used and is dissolved in aqueous formaldehyde maintained at a temperature higher than the polymerization point of the aqueous formaldehyde, whereupon the stabilizer is added and dissolved while still operating at the said temperature, whereupon the obtained solution may safely be cooled to room temperature.

The aqueous formaldehyde useful for dissolving the molten phenol advantageously has a formaldehyde content variable from 36 to 55% by weight, corresponding to a formaldehyde/water proportion of 0.56:1 to 1.22:1 in the composition according to this invention.

In the preferred embodiment use is made of pure or nearly pure phenol (titer 99% by weight or more) and of aqueous formaldehyde at a concentration of about 50 percent by weight, and in this case the aqueous formaldehyde heated at 50°–55° C. under agitation is additioned with molten phenol heated at the same range of temperature, and the stabilizer is added by operating at 40°–55° C.

In every case the dissolution of phenol in the aqueous formaldehyde is immediate or nearly immediate and it is convenient to cool to room temperature when also the stabilizer has been dissolved. Maintaining the solution at elevated temperature for a long time may indeed cause an exceedingly high degree of condensation between phenol and formaldehyde. Accordingly, it is convenient during mixing to not exceed temperatures of the order of 55° C.

Obviously, in the mixing, the amounts of the constituents are metered so as to fall in the range indicated hereinbefore for the final solution.

The solutions prepared in this manner are liquid at room temperature and lower, and present a viscosity value at 25° C. typically in the range from 3 to 20 mPa.s. The storage even for long time periods does not impair their reactivity. It has been noted that the content of free phenol and formaldehyde keeps practically unaltered with time and this circumstance indicates virtual absence of condensation phenomena during the period of storage.

The solutions according to the present invention are particularly useful for the preparation of "A-stage" phenolic resins used for the impregnation of Kraft paper in the manufacture of decorative laminates.

In the following experimental tests aqueous formaldehyde titrating 50% by weight was used, with a formic acid content of about 0.04% by weight and with a methanol content of about 1.6% by weight.

The formaldehyde was heated at 50° C. and stirred in a glass flask and was additioned at first with molten phenol of 100% purity heated at about 50° C., whereupon a molasses was dissolved therein titrating 70% by weight of carbohydrates, derived from treatment of maize for preparation of dextrose. The mass is maintained at 40°–50° C. for about 2 hours to assure complete dissolution of the molasses and then the solution was cooled to room temperature (20°–50° C.). Samples were taken of 500 g each, which were placed in closed flasks and the latter were kept in thermostatic baths at selected low temperatures. The samples were continuously kept under observation to discover any turbidity or precipitation and their content in free phenol and formaldehyde was determined at regular time intervals.

In the following Examples parts and percentages are by weight if not stated otherwise.

EXAMPLE 1

Following the procedure just described above a solution is prepared starting from 43 parts phenol, 47 parts formalin and 10 parts molasses. In the obtained solution the molar ratio phenol/formaldehyde results 0.58:1, the water content is 26.5 percent and formic acid content is below 0.04%.

The examination concerning stability yields the results shown in Table 1.

TABLE 1

| Time | 0° C. | | | 20° C. | | | 30° C. | | |
|---|---|---|---|---|---|---|---|---|---|
| | aspect | % HCHO | % phenol | aspect | % HCHO | % phenol | aspect | % HCHO | % phenol |
| 0 days | clear | 22,3 | 43 | clear | 22,3 | 43 | clear | 22,3 | 43 |
| 10 days | clear | 22,2 | | clear | 21,6 | | clear | 21,3 | |
| 20 days | clear | 22,1 | | clear | 21,4 | | clear | 20,5 | |
| 30 days | clear | 22,1 | 42,8 | clear | 21,2 | 42,3 | clear | 20,1 | |
| 40 days | clear | 22,0 | | clear | 21,2 | | clear | 19,5 | 41,6 |
| 50 days | clear | 21,9 | | clear | 21,1 | | clear | — | |
| 60 days | clear | 21,9 | 42,7 | clear | 21 | | clear | 18,1 | 40,1 |
| 70 days | clear | 21,8 | | clear | 20,9 | | | | |
| 80 days | clear | 21,8 | | clear | 20,8 | | | | |
| 90 days | clear | 21,8 | 42,6 | clear | 20,8 | 42,3 | | | |

EXAMPLE 2

A solution is prepared starting from 45 parts phenol, 49 parts formalin, and 6 parts of molasses. The data concerning stability are shown in Table 2.

TABLE 2

| Days | 0 | 10 | 20 | 30 |
|---|---|---|---|---|
| Temperature 30° C.: | | | | |
| Aspect | clear | clear | clear | clear |
| % HCHO | 24,4 | 24 | 23,1 | 21,5 |
| % phenol | 44,9 | — | — | 44 |
| Temperature 10° C.: | | | | |
| Aspect | clear | clear | clear | clear |
| % HCHO | 24,4 | 24,1 | 23,7 | 22,9 |
| % phenol | 44,9 | — | — | 44,4 |
| Temperature 0° C.: | | | | |
| Clouding after about 24 hours | | | | |

EXAMPLE 3

A solution is prepared starting from 46 parts phenol, 50 parts formalin, and 4 parts of molasses. The data concerning stability are shown in Table 3.

TABLE 3

| Days | 0 | 10 | 20 | 30 |
|---|---|---|---|---|
| Temperature 30° C. | | | | |
| Aspect | clear | clear | clear | clear |
| % HCHO | 24,4 | 24,1 | 23,6 | 23,3 |
| % phenol | 44,9 | — | — | 44,4 |
| Temperature 10° C.: | | | | |
| Aspect | clear | clear | clear | clear |
| % HCHO | 24,4 | 24,2 | 24,0 | 23,8 |
| % phenol | 44,9 | — | — | 44,6 |
| Temperature 0° C.: | | | | |
| Clouding after about 24 hours. | | | | |

EXAMPLE 4

A solution is prepared starting from 47 parts phenol, 51 parts formaldehyde and 2 parts molasses. The data concerning stability are shown in Table 4.

TABLE 4

| Days | 0 | 10 | 20 | 30 |
|---|---|---|---|---|
| Temperature 30° C. | | | | |
| Aspect | clear | clear | clear | clear |
| % HCHO | 25,3 | 25 | 24,5 | 24 |
| % phenol | 46,8 | — | — | 46,2 |
| Temperature 10° C.: | | | | |
| Aspect | clear | clear | clear | clear |
| % HCHO | 25,3 | 25,1 | 24,7 | 24,2 |
| % phenol | 46,8 | — | — | 46,3 |
| Temperature 0° C.: | | | | |
| Clouding after 24 hours. | | | | |

EXAMPLE 5

A phenolic "A-stage" resin is prepared, suitable for impregnating Kraft paper, from the solution of Example 1. More particularly, 1112 parts of the fresh solution are additioned with 16 parts of aqueous sodium hydroxide at 50% concentration and polymerization is effected at 100° C. for 40 minutes. The resin so obtained, after cooling and dilution with 117 parts of methanol, shows a dry matter content of 54.8 percent (determined by keeping 3 grams of the product at 135° C. for 3 hours), a density of 1.150 g/ml, a Brookfield viscosity at 20° C. equal to 75 mPa.s and a setting time of 10 minutes and 25 seconds, this last determination being carried out on a heated plate at 120° C.

After the dilution with methanol as above stated, the resinous composition showed a clear aspect.

EXAMPLE 6

The procedure is as in Example 5 utilizing the solution of Example 1 kept at 15° C. for 30 days. The resin obtained after dilution with 117 parts of methanol shows a dry matter content of 54.7%, a density of 1.150 g/ml, a Brookfield viscosity of 73 mPa.s and a setting time of 10 minutes and 23 seconds. After the above stated dilution with methanol the composition showed a clear aspect.

EXAMPLE 7 (COMPARATIVE)

A phenolic "A-stage" resin is prepared starting from 380 parts of phenol at 100% purity, 520 parts of aqueous formaldehyde at 50% concentration and 16 parts of aqueous sodium hydroxide of 50% strength. The mass is polymerized at 100° C. for 40 minutes and, after cooling, is diluted with 117 parts of methanol. The product so obtained shows a dry matter content of 54.6%, a density at 20° C. of 1.142, a Brookfield viscosity of 70 mPa.s and a setting time of 10 minutes and 15 seconds. After the above stated dilution with methanol the resinous composition showed a clear aspect.

From the foregoing Examples 5, 6 and 7 it is noticeable that the use of the solutions both fresh and stored, according to the present invention, leads to "A-stage" resins wholly similar to those obtainable by starting from the individual constituents phenol and formaldehyde.

We claim:

1. An aqueous, fluid, storage-fluid solution of phenol, formaldehyde and a stabilizer, wherein: the molar ratio of the phenol to the formaldehyde is from 0.5:1 to 1.3:1; the water content does not exceed 30% by weight; the stabilizer comprises a carbohydrate or a mixture of carbohydrates in a proportion of from 1 to 10% by weight; the solution being free from purposely added acids and bases and its content of any genetic formic acid being not greater than 0.04% by weight.

2. A solution according to claim 1, wherein the stabilizer is selected among saccharose, glucose, fructose, maltose, their mutual mixtures and their mixtures with polysaccharides.

3. A solution according to claim 1, wherein the stabilizer is selected among molasses and hydrolysates of maize.

4. A solution according to claim 1, wherein the molar ratio phenol/formaldehyde is in the range from 0.55:1 to 0.75:1 and the water content is from 20 to 30% by weight.

5. A solution according to claim 1, wherein the weight ratio formaldehyde: water is substantially 1:1.

6. A process for preparing a solution according to any one of claims 1 to 5, comprising the steps of: dissolving molten phenol in an aqueous solution of formaldehyde at a concentration of 36 to 55% by weight while keeping the latter solution at a temperature above the polymerization point of the aqueous formaldehyde, adding the stabilizer while still operating at the said temperature until complete dissolution of the stabilizer, and then cooling the obtained solution to room temperature.

7. A process according to claim 6, wherein: the molten phenol has a titer of at least 99% by weight and a temperature of 50°–55° C., the starting aqueous of formaldehyde solution contains about 50% by weight of formaldehyde and is kept at 50°–55° C.; and the stabilizer is added by operating at 40°–55° C.

* * * * *